United States Patent
Sekiguchi et al.

(10) Patent No.: US 9,137,986 B2
(45) Date of Patent: Sep. 22, 2015

(54) MIXED AGROCHEMICAL EMULSION COMPOSITION COMPRISING ORGANIC PHOSPHOROUS PESTICIDE AND CHLORPICRIN

(71) Applicant: ISHIHARA SANGYO KAISHA, LTD., Osaka (JP)

(72) Inventors: Mikio Sekiguchi, Ibaraki (JP); Takao Awazu, Shiga (JP)

(73) Assignee: ISHIHARA SANGYO KAISHA, LTD., Osaka (JP)

(*) Notice: Subject to any disclaimer, the term of this patent is extended or adjusted under 35 U.S.C. 154(b) by 0 days.

(21) Appl. No.: 14/350,272

(22) PCT Filed: Oct. 3, 2012

(86) PCT No.: PCT/JP2012/006319
§ 371 (c)(1),
(2) Date: Apr. 7, 2014

(87) PCT Pub. No.: WO2013/051243
PCT Pub. Date: Apr. 11, 2013

(65) Prior Publication Data
US 2014/0235589 A1    Aug. 21, 2014

(30) Foreign Application Priority Data
Oct. 7, 2011   (JP) ................. 2011-222464

(51) Int. Cl.
| *A01N 25/22* | (2006.01) |
| *A01N 57/32* | (2006.01) |
| *A01N 33/18* | (2006.01) |
| *A01N 57/08* | (2006.01) |
| *A01N 47/08* | (2006.01) |

(52) U.S. Cl.
CPC ............ *A01N 25/22* (2013.01); *A01N 33/18* (2013.01); *A01N 47/08* (2013.01); *A01N 57/08* (2013.01); *A01N 57/32* (2013.01)

(58) Field of Classification Search
USPC ...................................... 514/94, 92
See application file for complete search history.

(56) References Cited

FOREIGN PATENT DOCUMENTS

| JP | 08231303 |   | 9/1996 |   |
|----|----------|---|--------|---|
| JP | 2000336002 A | | 12/2000 | |
| JP | 2002029902 A | | 1/2002 | |
| JP | 2004250437 A | | 9/2004 | |
| JP | 2007269787 A | | 10/2007 | |
| JP | 2009235092 A | * | 10/2009 | ............. A01N 25/18 |
| WO | 03/011032 A1 | | 2/2003 | |

OTHER PUBLICATIONS

Machine translation of JP 2009235092 A, [retrieved on Feb. 26, 2015] Retrieved from the Internet.*

* cited by examiner

*Primary Examiner* — Kristin Vajda
(74) *Attorney, Agent, or Firm* — Greenblum & Bernstein, P.L.C.

(57) ABSTRACT

The present invention relates to a mixed agrochemical emulsion composition comprising: an organic phosphorous pesticide represented by formula (I)

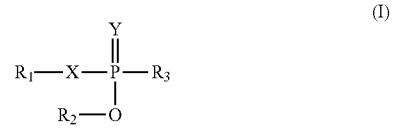

(wherein, $R_1$ represents a C1-4 linear or branched alkyl group; $R_2$ represents a C1-4 linear or branched alkyl group; $R_3$ represents a nitrogenated heterocyclic group which may have a substituent or a group —$OR_4$ (wherein $R_4$ represents a nitrogenated heterocyclic group which may have a substituent; and X and Y each independently represent an oxygen atom or a sulfur atom, wherein Y is a sulfur atom when X is an oxygen atom, and Y is an oxygen atom when X is a sulfur atom); chloropicrin; and a nonionic surfactant. The composition has excellent storage stability and excellent emulsifying properties in water and can be sprayed and applied conveniently by diluting the composition with water, in spite of a fact that both chloropicrin and the organic phosphorous pesticide, which are effective for the control of pests, are contained.

18 Claims, No Drawings

MIXED AGROCHEMICAL EMULSION COMPOSITION COMPRISING ORGANIC PHOSPHOROUS PESTICIDE AND CHLORPICRIN

CROSS-REFERENCES TO RELATED APPLICATIONS

This application is a 35 U.S.C. §371 U.S, national entry of International Application PCT/W2012/006319 (WO 2013/051243) having an International filing date of Oct. 3, 2012, which claims under 35 U.S.C. §119(a) the benefit of Japanese Application No. 2011-222464, filed Oct. 7, 2011, the entire contents of all of which applications are incorporated herein by reference.

TECHNICAL FIELD

The present invention relates to a mixed composition of chloropicrin and phosphoro- or phosphonothioate organic phosphorous pesticide containing a nitrogenated heterocyclic group and relates to a mixed emulsion composition that has excellent long-term storage stability and an excellent emulsifying property when it is mixed with water.

BACKGROUND ART

Among agricultural crops, the same crops are continuously cultivated in the same agricultural field in the facility cultivation of fruit vegetables, and flowers and ornamental plants. Therefore, disease-causing bacteria and Nematode adapted in the proximity to soil and the root areas of crops become to grow at a high concentration in those areas. And they invade to the root tissues of the crops resulting in generating root rot and root nodules, moreover they invade to the vessels of the crops and may lead to generate plant diseases on the parts of the plants above the ground. As a result, the growth of crops delays, and the yield and quality of the crops decrease having serious economical damage. Therefore, soil fumigants and pesticides have been using to control soilborne pathogens and harmful pests in soil.

Chloropicrin shows an insecticide-fungicide action, and has been widely used as a soil fumigant. It is a water immiscible liquid and volatile with odor. When a reagent is applied to treat the soil, a single-purpose disinfection apparatus for the soil is used by a method of infusing 2 to 3 mL of the reagent to the soil about 15 cm in deep and 30 cm intervals followed by coating the surface of the soil with coating materials. Since this method requires the cumbersome procedure of implanting pesticides into the ground, there was a demand of an easy-to-use and efficient application method. To respond to this requirement, according to Patent Document 1, a pesticide emulsion comprising chloropicrin in addition to surfactant was developed and the emulsion could be mixed with water and applied for spraying. Moreover, Patent Document 2 disclosed a simple-to-use and effective way to achieve insect pest control, in which pesticide emulsion comprising chloropicrin in addition to a surfactant was applied to treat the soils through drip irrigation tubes and spraying it with a liquid fertilizer mixer while diluting pesticide emulsion with water after installing the drip irrigation tubes on the surface of the soil followed by covering it with coating materials.

It has been reported that chloropicrin is applied by mixing it with an organic phosphorous pesticide in order to compensate the efficacy of insect pest control of chloropicrin, or to improve the pest control effect of soil. For example, a fumigant comprising a mixture of chloropicrin and diazinon is disclosed in Patent Document 3 showing improving the residual efficacy of insect pest control of diazinon. Moreover, Patent Document 4 describes that the mixed composition comprising chloropicrin and propetamphos or fosthiazate can simultaneously achieve insecticidal-bactericidal effect in soil and pest control effect on harmful pests growing aboveground. Since the mixed use of chloropicrin along with organic phosphorous pesticide is a drug formulation that can achieve excellent and efficient insect pest control of harmful pests, there is a demand for the development of a mixed preparation with easy-to-use.

On the contrary, several reports are published that the development of mixed preparations of organic phosphorous pesticides with several pesticides for the purpose of compensating and enforcing the efficacy of killing pests. Patent Document 5 discloses a mixed composition of organic phosphorus pesticide-nematicide comprising an organic phosphorus-type nematicides selected from fosthiazate, imicyafos, or cadusafos, and an organic phosphorus-type pesticide as active ingredients.

However, chloropicrin has a physical property that gradually releases its acid component during the storage so that has concern about acidolysis of components in the mixed preparation by mixed use with other active ingredients in other pesticides. Especially, the organic phosphorous pesticide has a physical property of acidolysis and hydrolysis. Therefore, it was difficult to guarantee long-term storage stability for a mixed pesticide preparation in a metal container that filled with the mixed agrochemical emulsion composition comprising chloropicrin and an organic phosphorous pesticide.

CITATION LIST

Patent Documents

Patent Document 1: JP 2002-29902 A
Patent Document 2: JP 2000-336002 A
Patent Document 3: JP 8-231303 A
Patent Document 4: JP 2004-250437 A
Patent Document 5: JP 2007-269787 A

SUMMARY OF INVENTION

Problems to be Solved by the Invention

An object of the present invention is to provide a mixed agrochemical emulsion composition comprising chloropicrin and organic phosphorous pesticide represented by the following formula (I), which has long-term storage stability and excellent emulsifiability after long-term storage, and is easy-to-use for spraying.

Means for Solving the Problems

The inventors have examined strenuously to solve problems described above and found that a mixed agrochemical emulsion composition prepared by mixing chloropicrin and an organic phosphorous pesticide having a nitrogenated heterocyclic group represented by the following formula (I) with a non-ionic surfactant, in particular, a non-ionic surfactant containing an aryl group showed inhibition of the degradation of the organic phosphorous pesticide implying possible long-term storage, an excellent emulsifying property after long-term storage and mixing with water, in other words found that both stability in long-term storage and excellent emulsifying property go together resulting in achieving the present invention.

Thus, this application presents the following invention as the summary.

(1) A mixed agrochemical emulsion composition comprising chloropicrin, a non-ionic surfactant, and an organic phosphorous pesticide represented by the following formula (I):

Formula (I)

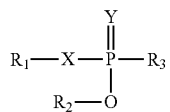

(wherein, $R_1$ represents a C1-4 linear or branched alkyl group; $R_2$ represents a C1-4 linear or branched alkyl group; $R_3$ represents a nitrogenated heterocyclic group which may have substituent(s); or a group —$OR_4$ (wherein $R_4$ represents a nitrogenated heterocyclic group which may have substituent(s)); and X and Y each independently represent an oxygen atom or sulfur atom, wherein either one of them is an oxygen atom and the other is a sulfur atom).

(2) The mixed agrochemical emulsion composition according to the above-mentioned item (1), wherein the nitrogenated heterocyclic group in $R_3$ or $R_4$ is an imidazolidinyl group, a 1,3-thiazolidinyl group, a 1,3-oxazolidinyl group, a pyrazolyl group, an isoxazolyl group, a thiazolyl group, a pyridyl group, a pyrimidyl group, or a pyridazinyl group.

(3) The mixed agrochemical emulsion composition according to the item (1) or (2) comprising: 0.1 to 80% by weight of the organic phosphorous pesticide, 10 to 90% by weight of chloropicrin, and 1 to 40% by weight of the non-ionic surfactant.

(4) The mixed agrochemical emulsion composition according to anyone of the items (1) to (3), wherein the organic phosphorous pesticide is selected from the group consisting of diazinon, fosthiazate, imicyafos, pyraclofos, chlorpyrifos and pirimiphos-methyl.

(5) The mixed agrochemical emulsion composition according to any one of the items (1) to (4), wherein the non-ionic surfactant is a non-ionic surfactant having a polyoxy C2-C4 alkylene aryl ether structure.

(6) The mixed agrochemical emulsion composition according to the item (5), wherein the non-ionic surfactant having a polyoxy C2-C4 alkylene aryl ether structure is polyoxy C2-C4 alkylene aryl ether or formaldehyde condensate thereof.

(7) The mixed agrochemical emulsion composition according to the item (5) or (6), wherein an aryl group in the polyoxy C2-C4 alkylene aryl ether structure is an unsubstituted phenyl group, a C8-C12 alkyl substituted phenyl group, or a phenyl group substituted with phenyl group(s) or phenyl group(s) substituted with C1-C3 aliphatic group(s).

(8) The mixed agrochemical emulsion composition according to any one of the items (5) to (7), wherein the non-ionic surfactant having a polyoxy C2-C4 alkylene aryl ether structure is polyoxy C2-C4 alkylene phenyl substituted phenyl ether, polyoxy C2-C4 alkylene benzyl substituted phenyl ether, polyoxy C2-C4 alkylene styryl substituted phenyl ether, or polyoxy C2-C4 alkylene (unsubstituted phenyl, C8-C12 alkyl substituted phenyl or styryl substituted phenyl) ether formaldehyde condensate.

(9) The mixed agrochemical emulsion composition according to the items (1) to (6), wherein the non-ionic surfactant is polyoxyethylene aryl ether or polyoxyethylene phenyl ether formaldehyde condensate.

(10) The mixed agrochemical emulsion composition according to any one of the above-mentioned items (1) to (4), wherein the non-ionic surfactant is polyoxy C2-C4 alkylene phenyl ether, polyoxy C2-C4 alkylene arylphenyl ether, any one of formaldehyde condensate thereof, or polyoxy C2-C4 alkylene C8-C12 alkyl substituted phenyl ether formaldehyde condensate.

(11) The mixed agrochemical emulsion composition according to the above-mentioned item (10), wherein the non-ionic surfactant is polyoxy C2-C4 alkylene phenyl ether formaldehyde condensate, or polyoxy C2-C4 alkylene arylphenyl ether, or formaldehyde condensate thereof.

(12) The mixed agrochemical emulsion composition according to any one of the items (1) to (11), further comprising epoxyglyceride or epoxidized vegetable oil.

(13) The mixed agrochemical emulsion composition according to the item (10), further comprising an anionic surfactant.

(14) The mixed agrochemical emulsion composition according to any one of the items (5) to (13), wherein a polyoxy C2-C4 alkylene part in the polyoxy C2-C4 alkylene aryl ether structure has from 10 to 25 repeating units, provided that, in the case that the non-ionic surfactant having a polyoxy C2-C4 alkylene aryl ether structure is polyoxy C2-C4 alkylene aryl ether formaldehyde condensate, two molecules are bound so that the number of repeating unit will be the sum of the number of repeating unit of the polyoxy C2-C4 alkylene parts.

(15) The mixed agrochemical emulsion composition according to anyone of the items (1) to (14), wherein the organic phosphorous pesticide is fosthiazate or imicyafos.

(16) The mixed agrochemical emulsion composition according to the above-mentioned item (1), wherein the organic phosphorous pesticide is fosthiazate or imicyafos, and the non-ionic surfactant is polyoxy C2-C4 alkylene arylphenyl ether, formaldehyde condensate thereof, or polyoxy C2-C4 alkylene phenyl ether formaldehyde condensate.

(17) The mixed agrochemical emulsion composition according to the above-mentioned item (16), wherein polyoxy C2-C4 alkylene arylphenyl ether is polyoxyethylene tristyrylphenyl ether, and polyoxy C2-C4 alkylene phenyl ether formaldehyde condensate is polyoxyethylene phenyl ether formaldehyde condensate.

(18) The mixed agrochemical emulsion composition according to any one of the above-mentioned items (15) to (17), further comprising epoxyglyceride or epoxidized vegetable oil.

(19) The mixed agrochemical emulsion composition according to the above-mentioned item (18), comprising: 0.3 to 10% by weight of fosthiazate or imicyafos, 70 to 90% by weight of chloropicrin, 5 to 30% by weight of polyoxy C2-C4 alkylene arylphenyl ether, formaldehyde condensate thereof, or polyoxy C2-C4 alkylene phenyl ether formaldehyde condensate, and 0.1 to 30% by weight of epoxyglyceride or epoxidized vegetable oil with respect to the total amount of the composition.

Advantageous Effects of the Invention

According to the present invention, despite the coexistence of the organic phosphorous pesticide, chloropicrin and the surfactant, the degradation of the unstable organic phosphorous pesticide was inhibited and the excellent storage stability for long-term was achieved. For example, after storage at 54° C. for 14 days, the residual ratio of the organic phosphorous pesticide represented by formula (I) is 80% and more, in particular, in the preferred case it is 90% and more. Moreover, the mixed preparation has excellent emulsifiability when it is mixed with water. In other words, the mixed agrochemical emulsion composition comprising the organic phosphorous pesticide represented by formula (I) and chloropicrin is in general possibly distributed as a mixed preparation. When the mixed preparation is applied, there is no need to mix the organic phosphorous pesticide and chloropicrin in use. To provide the mixed pesticide emulsion that allows the spraying pesticide effectively with water contributes tremendously to reduce agricultural work.

DESCRIPTION OF EMBODIMENTS

The present invention relates to a mixed agrochemical emulsion composition comprising an organic phosphorous pesticide having a specific chemical structure, chloropicrin, and a non-ionic surfactant. The present invention will be explained in detail below.

The mixed agrochemical emulsion composition in the present invention contains chloropicrin (trichloronitromethane) and an organic phosphorous pesticide represented by formula (I) as active ingredients.

Chloropicrin is water immiscible liquid with irritating odor, and has a physical property showing corrosive to metals. As chloropicrin used in the present invention, technical products of chloropicrin itself may be used, and a mixture thereof with a diluent such as kerosene and the like may be used.

An organic phosphorous pesticide used in the mixed agrochemical emulsion composition of the present invention is represented by the following formula (I):

Formula (I)

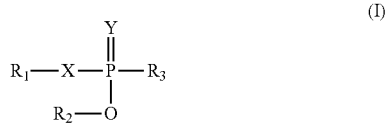

(I)

(wherein, $R_1$ represents a C1-4 linear or branched alkyl group; $R_2$ represents a C1-4 linear or branched alkyl group; $R_3$ represents a nitrogenated heterocyclic group which may have substituent(s) or a group of $-OR_4$ ($R_4$ represents a nitrogenated heterocyclic group which may have substituent(s)); and X and Y each independently represent an oxygen atom or a sulfur atom, wherein one of them is an oxygen atom and the other is a sulfur atom, in other words, X and Y never denote the same atom, when X is an oxygen atom, Y represents a sulfur atom, and when X is a sulfur atom, and Y represents an oxygen atom).

According to the present invention, the long-term storage stability of the organic phosphorous pesticide is guaranteed despite the coexistence of chloropicrin, the surfactant and the organic phosphorous pesticide with a specific structure in the emulsion in the present invention.

The $R_1$ or $R_2$ represents a C1-4 linear or branched alkyl group. The C1-4 linear or branched alkyl group refers to a methyl group, an ethyl group, an n-propyl group, an i-propyl group, an n-butyl group, an i-butyl group, a sec-butyl group, or a tert-butyl group, preferably a methyl group, an ethyl group or a propyl group.

Moreover, X and Y each independently represent an oxygen atom, or a sulfur atom. In this instance, X and Y never denote the same atom, when X is an oxygen atom, Y represents a sulfur atom, and when X is a sulfur atom, and Y represents an oxygen atom.

The $R_3$ represents a nitrogenated heterocyclic group, which may have substituent(s), or a group of $-OR_4$ ($R_4$ represents a nitrogenated heterocyclic group which may have substituent(s)). The nitrogenated heterocyclic groups as $R_3$ and $R_4$ refer to the same. Specifically, the nitrogenated heterocyclic group represents an imidazolidinyl group, a 1,3-thiazolidinyl group, a 1,3-oxazolidinyl group, a pyrazolyl group, an isoxazolyl group, a thiazolyl group, a pyridyl group, a pyrimidyl group, or a pyridazinyl group. Substituents, which may be on the nitrogenated heterocycle, are, for example, chlorine atom(s), oxo group(s), alkyl group(s) having 1 to 4 carbons, alkoxy group(s) having 1 to 4 carbons, phenyl group(s) that may be substituted with chlorine atom(s), cyanoimino group(s), and di(C1-C4) alkylamino group(s), and the like. Usually, a nitrogenated heterocyclic group having at least one substituent selected from the group consisting of these substituents is preferred.

More specifically, the nitrogenated heterocyclic group which may have the substituent as $R_3$ or $R_4$ includes a 5-phenylisoxazolyl group, a 2-oxo-1,3-thiazolidinyl group, a 2-(cyanoimino)-3-ethylimidazolidinyl group, a 1-(4-chlorophenyl)pyrazolyl group, a 3-methylpyrazolyl group, a 2,3,5-trichloropyridyl group, a 3-oxo-2-phenylpyridazinyl group, a pyrimidyl group, a 2-ethyl-4-ethoxypyrimidyl group, a 2-isopropyl-4-methylpyrimidyl group, and a 2-diethylamino-4-methylpyrimidyl group. Among them, a 2-oxo-1,3-thiazolidinyl group, a 2-(cyanoimino)-3-ethylimidazolidinyl group, or a 2-isopropyl-4-methylpyrimidyl group is preferred, a 2-oxo-1,3-thiazolidinyl group or 2-(cyanoimino)-3-ethylimidazolidinyl group is more preferred.

An organic phosphorous pesticide represented by formula (I) used in the present invention may be any organic phosphorous pesticide represented by formula (I) as long as having the property that active ingredient thereof kills harmful pests damaging roots and above-ground harmful pests. Commercialized products that are relevant to the organic phosphorous pesticide in the present invention can be used.

Specifically, O,O-dimethyl-O-(5-phenyl-3-isoxazolyl) phosphorothioate; (methyl isoxathion), O,O-diethyl-O-(5-phenyl-3-isoxazolyl)phosphorothioate; (isoxathion), O-ethyl S-propyl (E)-[2-(cyanoimino)-3-ethylimidazolidine-1-yl] phosphonothioate; (imicyafos), (RS)—(O-1-(4-chlorophenyl)pyrazole-4-yl)O-ethyl S-propyl phosphorothioate; (pyraclofos), (RS)—S-sec-butyl O-ethyl 2-oxo-1,3-thiazolidine-3-yl phosphonothioate; (fosthiazate), O,O-diethyl-O-3,5,6-trichloro-2-pyridyl phosphorothioate; (chlorpyrifos), O,O-diethyl O-6-oxo-1-phenyl-1,6-dihydro-3-pyridazinyl phosphorothioate; (pyridafenthion), O-6-ethoxy-2-ethyl pyrimidine-4-yl O,O-dimethyl phosphorothioate; (etrimfos), O,O-diethyl O-(2-isopropyl-6-methylpyrimidine-4-yl)phosphorothioate; (diazinon), and O-2-diethylamino-6-methylpyrimidine-4-yl O,O-dimethyl phosphorothioate; (pirimiphos-methyl) are included. These pesticides are commercially available and obtainable. Preferably, they are available under the name of diazinon, fosthiazate, imicyafos, pyraclofos, chlorpyrifos or pirimiphos-methyl as their general names. Diazinon, fosthiazate or imicyafos are more preferable.

From the perspective of the fact that the concomitant usage of those pesticides with chloropicrin can exterminate above-ground harmful pests as well as harmful pests within soil, preferable examples include O-ethyl S-propyl (E)-[2-(cyanoimino)-3-ethylimidazolidine-1-yl]phosphonothioate;

(imicyafos) or (RS)—S-sec-butyl O-ethyl 2-oxo-1,3-thiazolidine-3-yl phosphonothioate; (fosthiazate).

Moreover, from the standpoint of ability of pesticide providing the residual efficacy of insect pest control effect, the concomitant usage of chloropicrin and O,O-diethyl O-(2-isopropyl-6-methylpyrimidine-4-yl)phosphorothioate; (diazinon) is preferable.

Thus, in the present invention, as the organic phosphorous pesticide, O-ethyl S-propyl (E)-[2-(cyanoimino)-3-ethylimidazolidine-1-yl]phosphonothioate; (imicyafos), (RS)—S-sec-butyl O-ethyl 2-oxo-1,3-thiazolidine-3-yl phosphonothioate; (fosthiazate), and O,O-diethyl O-(2-isopropyl-6-methylpyrimidine-4-yl)phosphorothioate; (diazinon) are preferred.

The mixed agrochemical emulsion composition in the present invention contains a non-ionic surfactant. As the non-ionic surfactant, in particular, a non-ionic surfactant containing an aryl group is preferred and it can provide properties of long-term storage stability and excellent emulsifying to the mixed formulation of chloropicrin and the organic phosphorous pesticide represented by formula (I) at the same time. As the preferable non-ionic surfactant, a surfactant containing polyoxyalkylene aryl ether structure is included.

As the applicable non-ionic surfactant in the present invention, a non-ionic surfactant having the above-mentioned aryl group is preferred, in some cases; other non-ionic surfactants may be used.

As the above-mentioned non-ionic surfactant containing an aryl group, a surfactant having a polyoxyalkylene aryl ether structure, preferably a polyoxy C2-C4 alkylene aryl ether structure is included. As the surfactant, for example, polyoxy C2-C4 alkylene aryl ether or formaldehyde condensate thereof is included.

Specific examples of preferable polyoxy C2-C4 alkylene aryl ether include polyoxyethylene aryl phenyl ether such as polyoxyethylene mono- or tri-stylylphenyl ether and the like, or, polyoxyethylene alkylaryl ether (preferably polyoxyethylene C8-C12 alkylaryl ether, for example, polyoxyethylene nonylphenyl ether and the like). Moreover, specific examples of preferable above-mentioned formaldehyde condensate include formaldehyde condensate of the specific example of preferable above-mentioned polyoxy C2-C4 alkylene aryl ether, and, polyoxyethylene phenyl ether formaldehyde condensate.

Preferable specific examples of polyoxy C2-C4 alkylene aryl ether or formaldehyde condensate thereof include polyoxyethylene aryl phenyl ether such as polyoxyethylene mono- or tri-styrylphenyl ether and the like, or polyoxyethylene phenyl ether formaldehyde condensate.

Examples of non-ionic surfactant other than non-ionic surfactant containing an aryl group include, for example, block polymer of polyoxyethylene and polyoxyethylene, polyoxyethylene alkyl ether, polyoxyethylene lanolin alcohol, polyoxyethylene sorbitan fatty acid ester, polyoxyethylene glyceryl mono fatty acid ester, polyoxypropylene glycol mono fatty acid ester, polyoxyethylene sorbitol fatty acid ester, polyoxyethylene castor oil derivative, polyoxyethylene fatty acid ester, higher fatty acid glycerin ester, sorbitan fatty acid ester, polyoxyethylene fatty acid amide, alkylol amide, polyoxyethylene alkyl amine, polyoxyethylene octyl ether, polyoxyethylene dodecyl ether, polyoxyethylene oleyl ester, polyoxyethylene sorbitan monooleate, and the like, but it is not limited to these.

In the present invention, non-ionic surfactant may be used as a mixture of one or two and more types of surfactants.

Moreover, example of a surfactant having a polyoxyalkylene aryl ether structure that is a suitable non-ionic surfactant includes a non-ionic surfactant having a polyoxy C2-C4 alkylene aryl ether structure (more preferably, a non-ionic surfactant having a polyoxyethylene aryl ether structure). This is a surfactant with polyoxy C2-C4 alkylene chain (for example, polyoxyethylene, polyoxypropylene, polyoxybutylene and the like, preferably polyoxyethylene) as a hydrophilic group, and an aryl group (preferably an unsubstituted phenyl group, a C8-C12 alkyl substituted phenyl group, an aryl substituted phenyl group or an arylalkyl substituted phenyl group) as a hydrophobicity group, linked by ether linkage. Any non-ionic surfactant having this structure is included, but in particular not limited to. For example, polyoxy C2-C4 alkylene aryl ether or formaldehyde condensate thereof can be included.

As the aryl group in the above-mentioned polyoxy C2-C4 alkylene aryl ether structure, an unsubstituted phenyl group, or a substituted phenyl group, for example, an alkyl substituted phenyl group (preferably a C8-C12 alkyl substituted phenyl group), an aryl substituted or an aryl C1-C3 aliphatic group substituted phenyl group (more specifically, a phenyl group substituted with phenyl group(s) or phenyl C1-C3 aliphatic group(s), for example, a phenyl substituted phenyl group, a benzyl substituted phenyl group, or a styryl substituted phenyl group, and the like), an arylalkyl group, and a polycyclic aryl group such as a naphthyl group, and the like are included. Among them, as the aryl group, an unsubstituted phenyl group or an arylphenyl group (for example, an aryl substituted or an aryl C1-C3 aliphatic group substituted phenyl group) is preferred, and an arylphenyl group is more preferred. According to the present invention, "arylphenyl" includes both phenyl substituted with aryl group(s) such as phenyl group(s) and naphthyl group(s) and the like, and phenyl substituted with arylalkyl group(s) such as benzyl group (s), styryl group(s) and the like.

Examples of an aryl-substituted or an aryl C1-C3 aliphatic-group substituted phenyl group include, for example, a phenyl substituted phenyl group, a benzyl substituted phenyl group or a styryl substituted phenyl group, and a phenyl group substituted with styryl group(s) is more preferable. The number of substituents of a phenyl substituted phenyl group, a benzyl substituted phenyl group or a styryl substituted phenyl group, wherein the substituents are phenyl groups, benzyl groups or styryl groups, is 1 to 3, and any of mono-, di- or tri-phenyl, benzyl or styryl substituted phenyl group may be included. As the styryl substituted phenyl group, tri-styryl phenyl group is more preferable.

Moreover, in the case of a polyoxy C2-C4 alkylene aryl ether formaldehyde condensate, examples of a preferable aryl group include an unsubstituted phenyl group, a C8-C12 alkyl substituted phenyl group or a styryl substituted phenyl group, more preferably, an unsubstituted phenyl group.

Preferable examples of a non-ionic surfactant having a polyoxy C2-C4 alkylene aryl ether structure include polyoxy C2-C4 alkylene aryl ether or formaldehyde condensate thereof. Examples of polyoxy C2-C4 alkylene aryl ether include polyoxy C2-C4 alkylene unsubstituted or alkyl substituted phenyl ether such as polyoxy C2-C4 alkylene phenyl ether, polyoxy C2-C4 alkylene C8-C12 alkyl substituted phenyl ether and the like, and polyoxy C2-C4 alkylene arylphenyl ether such as polyoxy C2-C4 alkylene phenyl substituted phenyl ether, polyoxy C2-C4 alkylene benzyl substituted phenyl ether, or polyoxy C2-C4 alkylene mono- or tri-styryl substituted phenyl ether and the like, preferably polyoxy C2-C4 alkylene arylaryl ether such as polyoxy C2-C4 alkylene phenyl substituted phenyl ether, polyoxy C2-C4 alkylene benzyl substituted phenyl ether, or polyoxy C2-C4 alkylene styryl substituted phenyl ether. Also, "arylaryl" as polyoxy C2-C4 alkylene arylaryl ether represents the meaning of both aryl substituted aryl or aryl C1-C3 aliphatic group substituted aryl, more specifically means a phenyl substituted phenyl group, a benzyl substituted phenyl group or styryl substituted phenyl group, and the like.

Moreover, as polyoxy C2-C4 alkylene aryl ether formaldehyde condensate, polyoxy C2-C4 alkylene (unsubstituted phenyl, C8-C12 alkyl substituted phenyl, or arylphenyl, for example, mono- or tri-styryl substituted phenyl)ether formaldehyde condensate is preferred. For example, polyoxy C2-C4 alkylene phenyl ether formaldehyde condensate, polyoxy C2-C4 alkylene C8-C12 alkyl substituted phenyl ether formaldehyde condensate, or polyoxy C2-C4 alkylene styryl substituted phenyl ether formaldehyde condensate, and the like are included.

As the surfactant, examples of the phenyl substituted phenyl group, the benzyl substituted phenyl group or the styryl substituted phenyl group include mono-, di- or tri-phenylphenyl group, mono-, di- or tri-benzylphenyl group or mono-, di- or tri-styrylphenyl group.

Specific examples of the non-ionic surfactant having a polyoxy C2-C4 alkylene aryl ether structure include, for example, polyoxyethylene mono- or tri-styrylphenyl ether, polyoxyethylene phenyl ether formaldehyde condensate, poly oxyethylene nonylphenyl ether, and the like. Polyoxyethylene styrylphenyl ether, polyoxyethylene tristyrylphenyl ether or polyoxyethylene phenyl ether formaldehyde condensate is more preferable.

The number of the repeating unit of the polyoxy C2-C4 alkylene part in the non-ionic surfactant having a polyoxy C2-C4 alkylene aryl ether structure used in the present invention (specifically, oxy C2-C4 alkylene unit) is preferably from about 10 to 25, further preferably from about 12 to 20 with the object of emulsifiability of the composition in the present invention. In the case that the non-ionic surfactant having a polyoxy C2-C4 alkylene aryl ether structure is polyoxy C2-C4 alkylene aryl ether formaldehyde condensate, usually its structure mainly includes one having two molecules of polyoxy C2-C4 alkylene aryl ether linked by a methylene group, therefore, the number of the repeating unit will be the sum of the number of repeating unit of the both ethers. Moreover, a preferable range of HLB value of the non-ionic surfactant is from about 11 to 14.5, more preferably from about 11.5 to 13.5, further preferably from 12 to 13.4. When the HLB value of the non-ionic surfactant is within the range mentioned above, the surfactant shows more preferable property of emulsifying.

In the present invention, non-ionic surfactants having a polyoxy C2-C4 alkylene aryl ether structures, may be used alone or as a mixture of two and more surfactants, for example, 2 or 3 types of non-ionic surfactants may be mixed. For example, a mixture containing two and more types of polyoxyethylene aryl ether may be used. Moreover, in the present invention, the non-ionic surfactant having a polyoxy C2-C4 alkylene aryl ether structure, for example, the polyoxyethylene aryl ether may be concomitantly used with the other non-ionic surfactants. Usually, the non-ionic surfactant having a polyoxy C2-C4 alkylene aryl ether structure is preferably contained at least 50% and more by weight with respect to the total amount of the non-ionic surfactants, more preferably 75 to 100% by weight, further preferably 80 to 100% by weight. In light of storage stability of the organic phosphorous pesticide represented by formula (I), a non-ionic surfactant having a polyoxy C2-C4 alkylene aryl structure is preferably used alone, however, when the property of emulsifying is further needed to be improved, the anionic surfactant can be concomitantly used within an acceptable range of concentration in terms of the storage stability of the above-mentioned organic phosphorous pesticide. As the acceptable range of the concentration for the storage stability of the above-mentioned organic phosphorous pesticide, for example, the residual ratio of the above-mentioned organic phosphorous pesticide with respect to its initial concentration is 80% and more by liquid chromatography analysis, preferably 85% and more, further preferably 90% and more in storage stability study (store at 54° C. for 14 days) described below.

In the mixed agrochemical emulsion composition in the present invention, the composition ratio of each component is preferably 0.1 to 80% by weight of the organic phosphorous pesticide having nitrogenated heterocycle represented by formula (I), 10 to 90% by weight of chloropicrin, and 1 to 40% by weight of the non-ionic surfactant with respect to the total composition. Preferably, it is 0.1 to 20% by weight of the organic phosphorous pesticide represented by formula (I), 40 to 90% by weight of chloropicrin, and 5 to 30% by weight of the non-ionic surfactant with respect to the total amount of the composition. According to further preferable aspect, 0.3 to 10% by weight of the organic phosphorous pesticide represented by formula (I), 70 to 90% by weight of chloropicrin, and 5 to 30% by weight of a non-ionic surfactant (preferably a non-ionic surfactant having a polyoxy C2-C4 alkylene aryl ether structure) with respect to the total amount of the composition may be contained. When the organic phosphorous pesticide represented by formula (I) is fosthiazate or imicyafos, about 0.3 to 5% by weight (more preferably 0.3 to 3% by weight) of these with respect to the total amount of the composition may be used.

The mixed agrochemical emulsion composition of the present invention can be added to other components other than the above-mentioned components. As preferable additives, stabilizers, other surfactants, diluents, non-organic carries, and the like are included.

As the stabilizer that can be contained in the mixed agrochemical emulsion composition of the present invention, a component with a physical property that can capture free acid component released from chloropicrin is preferred. For example, (i) epoxyglyceride, (ii) epoxidized vegetable oils such as epoxidized soybean oil, epoxidized flaxseed oil, and the like, or (iii) alkaline agents such as soda lime, magnesium oxide, calcium oxide, and the like are included. Preferably, a component that can be dissolved in the chloropicrin and the organic phosphorous pesticide is preferred, and the use of epoxyglyceride or epoxidized soybean oil is preferred. One or two and more of these substances are concomitantly used, additive amount in the present invention is about 0 to 30% by weight, preferably 0.1 to 30% by weight, more preferably 0.1 to 20% by weight with respect to the total amount of the composition.

To the mixed emulsion composition in the present invention other surfactants can be added, if desired. As other surfactants, examples include surfactants other than the non-ionic surfactants used in the present invention. For example, an anionic surfactant, a cationic surfactant, an amphoteric surfactant and the like are included. When other surfactants are added, the stability of the organic phosphorous pesticide used in the present invention should be taken into consideration.

Addition of these other surfactants can be carried out, if desired, however, the addition of these surfactants generally gives disadvantage on the effect of the present, in particular, undesirable effect on the stability of the organic phosphorous pesticide used in the present invention. Therefore, it is preferable that these surfactants should not be added or minimizes the amount when they are added to in terms of the stability of the organophosphorus agent.

For example, the addition of anionic surfactants such as alkyl benzenesulfonic acid metallic salt (below, metallic salt represents alkali metal salt or alkali earth metal salt such as Na salt, Ca salt, and the like, a metallic salt of fatty acid such as Na salt of oleic acid and the like, a metallic salt of dialkyl ester of sulfosuccinic acid, a metallic salt of naphthalene-sulfonic acid polycondensate, a metallic salt of alkyl naphthalene sulfonic acid, a metallic salt of polycarboxylic acid, a metallic salt of polyoxyethylene alkylphenyl ether sulfate, and the like, often gives undesired effects on the stability of the organic phosphorous pesticide represented by formula (I), and, however, sometimes is preferable in terms of improving the emulsifiability of the composition in the present invention. For example, in some cases, emulsifiability of the composition in the present invention is improved, and the preparation of pesticide spray is simplified by the addition of anionic surfactants. If this is the case, the anionic surfactant can be added in such a way to minimize the disadvantageous effect on the organophosphorus agent, if desired.

Among the organic phosphorous pesticide represented by formula (I), fosthiazate or imicyafos leads adverse effect under the coexistence of chloropicrin and anionic surfactants, it is preferable to use the reduced amount of anionic surfactants as well as to use a stabilizing agent, when the anion surfactant is mixed.

The additive amount of the other surfactant in the present invention is preferably about 0 to 30% by weight with respect to the total amount of the composition in the present invention, when the addition is needed, preferably 0.1 to 30% by weight, more preferably 0.1 to 20% by weight with respect to the total amount of composition. The ratio of the anionic surfactant with respect to the total amount of the non-ionic surfactants used in the present invention is 0 to 50% by weight, preferably about 0 to 40% by weight.

In the present invention, when an anionic surfactant is used as other surfactant, the above-mentioned stabilizing agent such as epoxidized vegetable oil and the like is preferably concomitantly used.

Various favorite aspects of the mixed agrochemical emulsion composition in the present invention are included as follows:

(i) A mixed agrochemical emulsion composition comprising the organophosphorus agent represented by the formula (I), chloropicrin, and at least one non-ionic surfactant selected from the group consisting of polyoxy C2-C4 alkylene phenyl ether, polyoxy C2-C4 alkylene C8-C12 alkyl substituted phenyl ether and polyoxy C2-C4 alkylene arylphenyl ether, or formaldehyde condensate thereof.

(ii) The mixed agrochemical emulsion composition according to the above-mentioned item (i), wherein the non-ionic surfactant is polyoxy C2-C4 alkylene phenyl ether or an aldehyde condensate thereof, polyoxy C2-C4 alkylene arylphenyl ether or a formaldehyde condensate thereof, or a polyoxy C2-C4 alkylene C8-C12 alkyl substituted phenyl ether formaldehyde condensate.

(iii) The mixed agrochemical emulsion composition according to the above-mentioned item (ii), wherein polyoxy C2-C4 alkylene arylphenyl ether is polyoxy C2-C4 alkylene phenylphenyl ether or polyoxy C2-C4 alkylene phenyl C1-C3 aliphatic group substituted phenyl ether.

(iv) The mixed agrochemical emulsion composition according to the above-mentioned item (iii), wherein polyoxy C2-C4 alkylene phenyl C1-C3 aliphatic group substituted phenyl ether is polyoxy C2-C4 alkylene styryl substituted phenyl ether.

(v) The mixed agrochemical emulsion composition according to the above-mentioned (iv), wherein polyoxy C2-C4 alkylene styryl substituted phenyl ether is polyoxyethylene tristyrylphenyl ether.

(vi) The mixed agrochemical emulsion composition according to any one of the above-mentioned items (i) to (v), wherein the polyoxy C2-C4 alkylene phenyl ether formaldehyde condensate is polyoxyethylene phenyl ether formaldehyde condensate.

(vii) The mixed agrochemical emulsion composition according to any one of the above-mentioned items (i) to (vi) further comprising epoxyglyceride or epoxidized vegetable oil.

(viii) The mixed agrochemical emulsion composition according to the above-mentioned items (i) to (vi), comprising: 0.1 to 20% by weight of the above-mentioned organic phosphorous pesticide, 40 to 90% by weight of chloropicrin, and 5 to 30% by weight of the non-ionic surfactant with respect to the total amount of the composition, further, if desired, comprising 0 to 30% by weight of epoxyglyceride or epoxidized vegetable oil with respect to the total composition.

(ix) The mixed agrochemical emulsion composition according to any one of the above-mentioned items (i) to (viii), wherein the organic phosphorous pesticide is at least one selected from the group consisting of diazinon, fosthiazate and imicyafos.

(x) The mixed agrochemical emulsion composition according to the above-mentioned item (ix), wherein the organic phosphorous pesticide is fosthiazate or imicyafos.

(xi) The mixed agrochemical emulsion composition according to the above-mentioned item (viii), comprising: 0.3 to 10% by weight the above-mentioned organic phosphorous pesticide, 70 to 90% by weight of choloropicrin, 5 to 30% by weight of polyoxy C2-C4 alkylene arylphenyl ether or formaldehyde condensate thereof, or polyoxy C2-C4 alkylene phenyl ether formaldehyde condensate, and 0.1 to 30% by weight of epoxyglyceride or epoxidized vegetable oil with respect to the total amount of the composition, wherein the organic phosphorous pesticide is fosthiazate or imicyafos.

(xii) The mixed agrochemical emulsion composition according to any one of the above-mentioned items (i) to (xi), wherein a polyoxy C2-C4 alkylene group of the above-mentioned non-ionic surfactant has from 10 to 25 repeating unit (oxy C2-C4 alkylene unit).

(xiii) The mixed agrochemical emulsion composition according to any one of the above-mentioned items (i) to (xii), wherein the range of HLB values of the above-mentioned non-ionic surfactant is from 11 to 14.5.

A diluent is not particularly limited as long as it can arbitrarily be mixed with chloropicrin and organic phosphorous pesticide containing the nitrogenated heterocycle, and publicly known diluents can be used. Specific examples include kerosene (white kerosene, kerosene for fuel, solvent kerosene, kerosene for lamp, and the like), petroleum naphtha, petroleum spirit, toluene, xylene, ethylbenzene, and the like. Preferably kerosene is used, further preferably white kerosene is used. One or two and more kinds of those may be concomitantly used. Moreover, additional amount is not in particular limited; any amount may be added, if desired. The additional amount with respect to the total amount of the composition in the present invention is from about 0 to 60% by weight, which can be arbitrarily selected. Usually, it is from about 0 to 30% by weight.

According to a preferable aspect, the residual ratio of the organic phosphorous pesticide represented by formula (I) in the composition of the present invention is 80% and more by liquid chromatography analysis after storing at 54° C. for 14 days, preferably 85% or more, more preferably 88% or more, further preferably 90% or more, the most preferably 95% or more.

The treatment method of the agrochemical emulsion composition of the present invention to soil can lead to insect pest control effect by diluting the agrochemical emulsion composition of the present invention with water to prepare a pesticide spray solution and spraying the solution to agricultural field. Generally, chloropicrin formulation for the use of soil fumigation is infused with constant amount at regular interval of about 30 cm to the entire agricultural field, so that it has required a lot of labor and time. Pesticide emulsion of the present invention shows excellent property of emulsifying and can be sprayed by using water; therefore, it provides easy-to-use and efficient pesticide spray. In particular, preferable spraying method is a method of spraying the composition of the present invention by installing drip irrigation tubes to the surface of soil or within soil, and covering the soil surface with coating materials, and spraying the composition passing through the drip irrigation tubes with a liquid fertilizer mixer etc., while diluting it with 10 to 300-times volume of water.

As the drip irrigation tubes used, for example, commercially available drip irrigation tubes (watering tube) and drip infusion tubes, and any tubes such as tubes with holes at lateral sides can be used. Tubes without holes, for example, pipes such as tap water hoses, vinyl chloride tap water pipes, drainpipes can be used by adding holes thereto.

As the materials of the drip irrigation tubes, one or two and more types of copolymerized materials and mixtures of polyethylene, polyvinyl chloride, fluoro resin, silicon resin, polypropylene, nylon, and polypropylene may be used, but not limited to, unless not being degenerated by exposing temperature stress or contacting with the pesticide used or soil water. The suitable diameter of the drip irrigation tube, but not particularly limited to, is about 1 mm to 300 mm in diameter. When the diameter of the hole of the drip irrigation tube is too big, the large amount of water is needed, or when it is too small, it requires too long for pesticide treatment. Therefore, holes are preferable from 0.1 μm to 30 mm in diameter, and suitable from about 1 μm to 10 mm. The holes on the tube may be opened at lateral sites, at the equal intervals from 10 to 200 cm or one or two rows randomly, or opened circumference of the whole surface, but not limited to these.

As irrigation method by drip irrigation tubes, for example, drip irrigation-type, aerosol-type, porous-type, water spraying type, and the like, are included, wherein the method are arbitrarily chosen depending on circumstances such as the width of spraying area and the shape of agricultural field. As the drip irrigation tubes, for example, EVER FLOW A, SUPER EVER FLOW A-100, EVER FLOW M (aerosol-type), EVER FLOW D (drip irrigation-type), EVER FLOW S (water-spraying-type), EVER FLOW KW (one-side water-spraying-type), KIRICO BIG HOLE SIDE SPRAY, KIRIKO A type, KIRIKO (multi) type, KIRIKO H type (for indoor), KIRIKO R type, KIRIKO KH type, KIRIKO H type, one-side water-spraying-type, STRONG P.E drip irrigation tube, CHAPIN drip irrigation tube (watering tube, manufactured by Mitsui Chemicals Co., Ltd.), SUMISANSUI MULTI (Sumitomo Chemical Co., Ltd.), ONE-SIDE HOLE-TYPE DRIP IRRIGATION TUBE (manufactured by Nisshin Chemical Industry Co., Ltd.), SAFETY DRIP IRRIGATION TUBE or DRIP IRRIGATION POWER S TUBE (manufactured by Itochu Sanplus Co., Ltd.), and the like can be use, but not limited to these.

In the present invention, the area for installing drip irrigation tubes is not in particular limited, as long as it is in soil surface or within soil, and the soil surface or within soil inside a horticultural facility is preferable. Examples of the horticultural facility, include a tunnel for tunnel culture, a vinyl greenhouse, a glass greenhouse, and the like. After installing the drip irrigation tubes, the soil surface is covered with coating materials, if desired. When the soil surface is covered with coating materials, the coating materials are removed from the area where plants are supposed to be planted, and then the plants are planted and cultivated. In horticultural facilities, the soil surface is often covered with coating materials. In the present invention, pesticide is sprayed after harvesting crops. However, in light of the improvement of weed killing effect and enhancement of pest control effect against harmful pests, spraying pesticide in the closed horticultural facilities is preferred when a volatile active ingredient for pesticide is used as an active ingredient.

As a coating material used in the present invention, a film having gas barrier property is preferred. Among them, any coating film having gas barrier property can be used in the case of pesticide treatment with high vapor pressure, but not particularly limited to. The gas barrier property varies depending on the properties of films themselves, the thickness of the film, or the combination of films used in multi layered film made from several various films. As the coating film, the strength of coating material for covering soil and economic efficiency should be definitely taken into consideration, however, higher gas barrier property is preferred, and oxygen gas permeability (the condition and method to measure gas permeability is at 25° C. and at 50% of relative humidity according to ASTMD1434-66, and with respect to the film thickness, calculation for correcting inverse proportion is conducted with the thickness of film measured as a standard) is usually 8000 cc/m$^2$·hr·atm or less, preferably 4000 cc/m$^2$·hr·atm or less.

As the quality of material of the film, for example, the film including copolymer or a mixture of one or two and more kinds of materials selected from polyethylene terephthalate, polyamide resin, nylon, polyvinylidene chloride, polyvinyl chloride, polyacrylonitrile, polyvinyl alcohol, ethylene-vinyl alcohol copolymerized material, polyethylene, ethylene-vinyl acetate polymeric substance, polypropylene, and the like, or a multi-layered film thereof are selected, but not limited to.

The thickness of the film is associated with oxygen gas barrier property. A single layer film such as polyethylene and soft vinyl chloride that does not have enough gas barrier property is required to be thickened for improving gas barrier property considering that gas permeability is inversely proportional to the thickness. Moreover, a film with easy-to-use and excellent economic efficiency, which does not degenerate such as losing gas barrier property by contacting pesticides used and soil water, is required to be used. The preferred thickness is generally from 10 μm to 500 μm, suitably from 10 μm to 200 μm, however, it depends on various materials.

EXAMPLES

The present invention will be explained in detail by examples, but not limited to as long as it is within the spirit and scope of the present invention.

Example 1

Eighty parts by mass of chloropicrin, 0.7 parts by mass of fosthiazate, and 19.3 parts by mass of polyoxyethylene tristyrylphenyl ether (trade name; SORPOL T-15 manufactured by TOHO Chemical Industry Co., Ltd., the number of ethylene oxide addition moles, 14; HLB, 12.0) were mixed and stirred to obtain a mixed agrochemical emulsion composition of the present invention.

Example 2

Eighty parts by mass of chloropicrin, 0.7 parts by mass of fosthiazate, and 17.3 parts by mass of polyoxyethylene tristyrylphenyl ether (trade name; SORPOL T-15, manufactured by TOHO Chemical Industry Co., Ltd.), and 2 parts by mass of epoxyglyceride (trade name; K-800 manufactured by TAKEMOTO OIL & FAT CO., Ltd.) were mixed and stirred to obtain a mixed agrochemical emulsion composition of the present invention.

Example 3

Eighty parts by mass of chloropicrin, 0.7 parts by mass of fosthiazate, 11.3 parts by mass of polyoxyethylene tristyrylphenyl ether (trade name; SORPOL T-15, manufactured by TOHO Chemical Industry Co., Ltd.), and 8 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 4

Eighty parts by mass of chloropicrin, 0.7 parts by mass of fosthiazate, and 10.3 parts by mass of polyoxyethylene tristyrylphenyl ether (trade name; SORPOL T-15, manufactured by TOHO Chemical Industry Co., Ltd.), 7 parts by mass of kerosene, and 2 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 5

Eighty parts by mass of chloropicrin, 0.7 parts by mass of fosthiazate, 17.3 parts by mass of polyoxyethylene phenyl ether formaldehyde condensate (trade name; NEW KALGEN D-615; HLB, 12.0; manufactured by TAKEMOTO OIL & FAT CO., Ltd.), and 2 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 6

Eighty of parts by mass of chloropicrin, 0.7 parts by mass of fosthiazate, 11.3 parts by mass of polyoxyethylene phenyl ether formaldehyde condensate (trade name; NEW KALGEN D-615, manufactured by TAKEMOTO OIL & FAT CO., Ltd.), and 8 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 7

Eighty of parts by mass chloropicrin, 0.7 parts by mass fosthiazate, 4 parts by mass of dodecyl benzenesulfonic acid calcium salt (anion-type surfactant, trade name; RHODACAL60/BE; HLB 8.3; Rhodia Nikka Co., Ltd.), 13.3 parts by mass of polyoxyethylene tristyrylphenyl ether (trade name; SORPOL T-15, manufactured by TOHO Chemical Industry Co., Ltd.) and 2 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 8

Eighty parts by mass of chloropicrin, 0.7 parts by mass of fosthiazate, 17.3 parts by mass of polyoxyethylene tristyrylphenyl ether (trade name; SORPOL T-20, the number of ethylene oxide addition moles, 19; HLB, 13.3; manufactured by TOHO Chemical Industry Co., Ltd.), and 2 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 9

Eighty parts by mass of chloropicrin, 0.7 parts by mass of fosthiazate, 17.3 parts by mass of polyoxyethylene tristyrylphenyl ether (trade name; SOPROFOL CY/8, the number of ethylene oxide addition moles, 20; HLB, 13.5; Rhodia Nikka CO., Ltd.), and 2 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 10

Eighty parts by mass of chloropicrin, 0.7 parts by mass of fosthiazate, 17.3 parts by mass of polyoxyethylene tristyrylphenyl ether (trade name; SOPROFOL S/25, the number of ethylene oxide addition moles 25, HLB 14.5, Rhodia Nikka CO., Ltd.), and 2 parts by mass epoxyglyceride (trade name; K-800, manufactured by TAKEMOTO OIL & FAT CO., Ltd.) were mixed and stirred to obtain a mixed agrochemical emulsion composition of the present invention.

Example 11

Eighty parts by mass of chloropicrin, 2 parts by mass of diazinon, and 18 parts by mass of polyoxyethylene phenyl ether formaldehyde condensate (trade name; NEW KALGEN D-615, manufactured by TAKEMOTO OIL & FAT CO., Ltd.) were mixed and stirred to obtain a mixed agrochemical emulsion composition of the present invention.

Example 12

Eighty parts by mass of chloropicrin, 2 parts by mass of diazinon, 16 parts by mass of polyoxyethylene phenyl ether formaldehyde condensate (trade name; NEW KALGEN D-615, manufactured by TAKEMOTO OIL & FAT CO., Ltd.), and 2 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 13

Eighty parts by mass of chloropicrin, 2 parts by mass of diazinon, 10 parts by mass of polyoxyethylene phenyl ether formaldehyde condensate (trade name; NEW KALGEN D-615, manufactured by TAKEMOTO OIL & FAT CO., Ltd.), and 8 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 14

Seventy parts by mass of chloropicrin, 2 parts by mass of diazinon, 18 parts by mass of polyoxyethylene phenyl ether formaldehyde condensate (trade name; NEW KALGEN D-615, manufactured by TAKEMOTO OIL & FAT CO., Ltd.), and 10 parts by mass of kerosene were mixed and stirred to obtain a mixed agrochemical emulsion composition of the present invention.

Example 15

Seventy parts by mass of chloropicrin, 2 parts by mass of diazinon, 10 parts by mass of polyoxyethylene phenyl ether formaldehyde condensate (trade name; NEW KALGEN D-615, manufactured by TAKEMOTO OIL & FAT CO., Ltd.), 10 parts by mass of kerosene, and 8 parts by mass of epoxyglyceride (trade name; K-800, manufactured by TAKEMOTO OIL & FAT CO., Ltd.) were mixed to obtain a pesticide composition of the present invention.

Example 16

Eighty parts by mass of chloropicrin, 2 parts by mass of diazinon, and 18 parts by mass of NEW KALGEN KC-80 as a surfactant (trade name; a mixture of dodecyl benzenesulfonic acid metallic salt (anionic surfactant) and polyoxy C2-C4 alkylene arylphenyl ether (non-ionic surfactant) (mass ratio 1:2.64, including 20% by weight of solvent, HLB 12.8, manufactured by TAKEMOTO OIL & FAT CO., Ltd.)] were mixed and stirred to obtain a mixed agrochemical emulsion composition of the present invention.

Example 17

Eighty parts by mass of chloropicrin, 2 parts by mass of diazinon, 16 parts by mass of NEW KALGEN KC-80 as a surfactant (trade name; a mixture of dodecyl benzenesulfonic acid metallic salt (anionic surfactant) and polyoxy C2-C4 alkylene arylphenyl ether (non-ionic surfactant) manufactured by TAKEMOTO OIL & FAT CO., Ltd.), and 2 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 18

Eighty parts by mass of chloropicrin, 2 parts by mass of diazinon, 10 parts by mass of NEW KALGEN KC-80 as a surfactant (trade name; a mixture of dodecyl benzenesulfonic acid metallic salt (anionic surfactant) and polyoxy C2-C4 alkylene arylphenyl ether (non-ionic surfactant), manufactured by TAKEMOTO OIL & FAT CO., Ltd.), and 8 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 19

Seventy parts by mass of chloropicrin, 2 parts by mass of diazinon, 10 parts by mass of NEW KALGEN KC-80 as a surfactant (trade name, a mixture of dodecyl benzenesulfonic acid metallic salt (anionic surfactant) and polyoxy C2-C4 alkylene arylphenyl ether (non-ionic surfactant), manufactured by TAKEMOTO OIL & FAT CO., Ltd.), 10 parts by mass of kerosene, and 8 parts by mass of epoxyglyceride (trade name; K-800, manufactured by TAKEMOTO OIL & FAT CO., Ltd.) were mixed and stirred to obtain a mixed pesticide composition of the present invention.

Example 20

Eighty parts by mass of chloropicrin, 0.7 parts by mass of imicyafos, and 19.3 parts by mass of polyoxyethylene tristyrylphenyl ether (trade name; SORPOL T-15, manufactured by TOHO Chemical Industry Co., Ltd.) were mixed and stirred to obtain a mixed agrochemical emulsion composition of the present invention.

Example 21

Eighty parts by mass of chloropicrin, 0.7 parts by mass of imicyafos, 17.3 parts by mass of polyoxyethylene tristyrylphenyl ether (trade name; SORPOL T-15, manufactured by TOHO Chemical Industry Co., Ltd.), and 2 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 22

Eighty parts by mass of chloropicrin, 0.7 parts by mass of imicyafos, 11.3 parts by mass of polyoxyethylene tristyrylphenyl ether (trade name; SORPOL T-15, manufactured by TOHO Chemical Industry Co., Ltd.), and 8 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 23

Eighty parts by mass of chloropicrin, 0.7 parts by mass of imicyafos, and 19.3 parts by mass of polyoxyethylene phenyl ether formaldehyde condensate (trade name; NEW KALGEN D-615, manufactured by TAKEMOTO OIL & FAT CO., Ltd.) were mixed and stirred to obtain a mixed agrochemical emulsion composition of the present invention.

Example 24

Eighty parts by mass of chloropicrin, 0.7 parts by mass of imicyafos, 17.3 parts by mass of polyoxyethylene phenyl ether formaldehyde condensate (trade name; NEW KALGEN D-615, manufactured by TAKEMOTO OIL & FAT CO., Ltd.), and 2 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 25

Eighty parts by mass of chloropicrin, 0.7 parts by mass of imicyafos, 11.3 parts by mass of polyoxyethylene phenyl ether formaldehyde condensate (trade name; NEW KALGEN D-615, manufactured by TAKEMOTO OIL & FAT CO., Ltd.), and 8 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 26

Eighty parts by mass of chloropicrin, 0.7 parts by mass of imicyafos, 17.3 parts by mass of NEW KALGEN KC-80 as a surfactant (trade name, a mixture of dodecyl benzenesulfonic acid metallic salt (anionic surfactant) and polyoxy C2-C4 alkylene arylphenyl ether (non-ionic surfactant), manufactured by TAKEMOTO OIL & FAT CO., Ltd.), and 2 parts by mass of epoxyglyceride (trade name; K-800, manufactured by TAKEMOTO OIL & FAT CO., Ltd.) were mixed and stirred to obtain a mixed agrochemical emulsion composition of the present invention.

Example 27

Eighty parts by mass of chloropicrin, 0.7 parts by mass of imicyafos, 11.3 parts by mass of NEW KALGEN KC-80 as a surfactant (trade name, a mixture of dodecyl benzenesulfonic acid metallic salt (anionic surfactant) and polyoxy C2-C4 alkylene arylphenyl ether (non-ionic surfactant), manufactured by TAKEMOTO OIL & FAT CO., Ltd.), and 8 parts by mass of epoxyglyceride (trade name; K-800, manufactured by TAKEMOTO OIL & FAT CO., Ltd.) were mixed and stirred to obtain a mixed agrochemical emulsion composition of the present invention.

Comparative Example 1

Eighty parts by mass of chloropicrin, 0.7 parts by mass of fosthiazate, 17.3 parts by mass of dodecyl benzenesulfonic acid calcium salt (anion-type surfactant, trade name; RHODACAL60/BE), and 2 parts by mass of epoxyglyceride (trade name; K-800, manufactured by TAKEMOTO OIL & FAT CO., Ltd.) were mixed and stirred to obtain a mixed agrochemical emulsion composition of the Comparative Example.

Comparative Example 2

Eighty parts by mass of chloropicrin, 0.7 parts by mass of imicyafos, and 19.3 parts by mass of dodecyl benzenesulfonic acid calcium salt (anion-type surfactant, trade name; NEW KALGEN A-85C, HLB, 7.0; manufactured by TAKEMOTO OIL & FAT CO., Ltd.) were mixed and stirred to obtain a mixed agrochemical emulsion composition of the Comparative Example.

Comparative Example 3

Eighty parts by mass of chloropicrin, 0.7 parts by mass of imicyafos, 17.3 parts by mass of dodecyl benzenesulfonic acid calcium salt (anion-type surfactant, trade name; NEW KALGEN A-85C, manufactured by TAKEMOTO OIL & FAT CO., Ltd.), and 2 parts by mass of epoxyglyceride (trade name; K-800, manufactured by TAKEMOTO OIL & FAT CO., Ltd.) were mixed and stirred to obtain a mixed agrochemical emulsion composition of the Comparative Example.

Comparative Example 4

Eighty parts by mass of chloropicrin, 0.7 parts by mass of imicyafos, 11.3 parts by mass of dodecyl benzenesulfonic acid calcium salt (anion-type surfactant, trade name; NEW KALGEN A-85C, manufactured by TAKEMOTO OIL & FAT CO., Ltd.), and 8 parts by mass of epoxyglyceride (trade name; K-800, manufactured by TAKEMOTO OIL & FAT CO., Ltd.) were mixed and stirred to obtain a mixed agrochemical emulsion composition of the Comparative Example.

Test Example 1

Stability Test of Formulations and Emulsifiability of the Formulations after the Stability Test Each mixed agrochemical emulsion composition (emulsion composition comprising chloropicrin and each organic phosphorous pesticide) in Examples 1 to 27 and Comparative Examples 1 to 4 was stored at 54° C. for 14 days, then the storage stability of each emulsion composition was examined.

Residual amount of chloropicrin, fosthiazate, diazinon, and imicyafos in each mixed pesticide emulsion in Examples 1 to 7 and 11 to 27, and Comparative Examples 1 to 4 was analyzed by liquid chromatography. The results from the analyses were shown in Tables 1 to 3. As the amount of each ingredient in the mixed pesticide before the test was referred to as 100, the amount of each ingredient in the emulsion after the test was listed in Tables 1 to 3 as a relative amount with respect to the amount before the test.

In addition to this, the appearances of the mixed agrochemical emulsion composition in Examples 1 to 27 and Comparative Examples 1 to 4 after the test were observed and confirmed whether the emulsion was clouded, and the results were listed in Tables 1 to 3. Moreover each of the formulations was sampled in volumetric flask with ground-in stopper after the test, then it was diluted with water by 100-fold and shook, the property of its emulsifying was tested and the evaluation of emulsifiability was carried out according to the following criterion. The results are listed in Tables 1 to 3.

Criteria of emulsifiability

○: content becomes homogeneous emulsion

Δ: a part of the agent adheres to the interior wall of a container x: the agent adheres to the interior wall of a container resulting in no emulsified condition

TABLE 1

Result of test for stability of mixed preparations of chloropicrin-fosthiazate

| Sample | Residual ratio of each ingredient after treating at 54° C. for 14 days | | Appearance | Emulsifiability |
|---|---|---|---|---|
| | Chloropicrin | Fosthiazate | | |
| Example 1 | 99.4 | 89.9 | Transparent | ○ |
| Example 2 | 100.0 | 95.2 | Transparent | ○ |
| Example 3 | 99.9 | 100.0 | Transparent | ○ |
| Example 4 | 100.0 | 100.0 | Transparent | ○ |
| Example 5 | 100.0 | 96.0 | Transparent | ○ |
| Example 6 | 100.0 | 96.0 | Transparent | ○ |
| Example 7 | 100.0 | 84.5 | Transparent | ○ |
| Example 8 | Unadministered | Unadministered | Transparent | ○ |
| Example 9 | Unadministered | Unadministered | Transparent | ○ |
| Example 10 | Unadministered | Unadministered | Transparent | ○ |
| Comparative Example 1 | 99.7 | 69.7 | Cloudy | X |

TABLE 2

Result of stability test of mixed preparations of chloropicrin-diazinon

| Sample | Residual ratio of each ingredient after treating at 54° C. for 14 days | | Appearance | Emulsifiability |
|---|---|---|---|---|
| | Chloropicrin | Diazinon | | |
| Example 11 | 98.6 | 88.9 | Transparent | ○ |
| Example 12 | 99.3 | 98.5 | Transparent | ○ |
| Example 13 | 99.6 | 99.5 | Transparent | ○ |
| Example 14 | 98.2 | 87.1 | Transparent | ○ |
| Example 15 | 98.0 | 100.0 | Transparent | ○ |
| Example 16 | 99.1 | 73.1 | Transparent | ○ |
| Example 17 | 99.1 | 97.0 | Transparent | ○ |
| Example 18 | 99.5 | 98.6 | Transparent | ○ |
| Example 19 | 98.0 | 96.6 | Transparent | ○ |

TABLE 3

Result of stability test of mixed preparations of chloropicrin-imicyafos

| Sample | Residual ratio of each ingredient after treating at 54° C. for 14 days | | Appearance | Emulsifiability |
|---|---|---|---|---|
| | Chloropicrin | Imicyafos | | |
| Example 20 | 98.2 | 80.8 | Transparent | ○ |
| Example 21 | 98.6 | 93.0 | Transparent | ○ |
| Example 22 | 99.4 | 97.2 | Transparent | ○ |
| Example 23 | 100.0 | 81.8 | Transparent | ○ |
| Example 24 | 99.2 | 98.6 | Transparent | ○ |
| Example 25 | 100.0 | 97.2 | Transparent | ○ |
| Example 26 | 99.7 | 87.1 | Transparent | ○ |
| Example 27 | 99.7 | 87.3 | Transparent | ○ |
| Comparative Example 2 | 100.0 | 48.6 | Transparent | X |
| Comparative Example 3 | 98.5 | 62.9 | Transparent | X |
| Comparative Example 4 | 100.0 | 71.4 | Transparent | X |

From these results, it was found that in the mixed agrochemical emulsion composition (Examples) of the present invention, there are a little degradation of fosthiazate, diazinon, or imicyafos that is an organophosphorus agent represented by formula (I), and the ingredients of the organic phosphorous pesticide has excellent stability. Moreover, the mixed agrochemical emulsion composition in the present invention presented the results showing excellent property of emulsifying after the stability test described above. On the other hand, in Comparative Examples using an anion-type surfactant as a surfactant, although the degradation of organophosphorus agent is suppressed by adding epoxyglyceride as a stabilizing agent less than that without the stabilizing agent, the degradation of the organic phosphorous pesticide was still observed. In particular, when fosthiazate or imicyafos is used as an organic phosphorous pesticide and formulated with addition of the anion-type surfactant, even with the addition of epoxyglyceride as a stabilizing agent, it showed difficulty to inhibit the degradation, as obvious from the results for Comparative Examples 1, 3 and 4, and it was difficult to guarantee the stability of the formulation which can tolerate in general distribution. From these results, the mixed agrochemical emulsion composition of the present invention has excellent property of emulsifying by mixing with water after long-term storage and excellent stability of the formulation as well as excellent stability of the components of the organic phosphorus pesticide. Therefore, the mixed agrochemical emulsion composition of the present invention possesses physical property of pesticide formulation that can be tolerable in general distribution.

INDUSTRIAL APPLICABILITY

The present invention enables admixture of chloropicrin and an organophosphorus-type pesticide represented by formula (I) as emulsion to use in drip irrigation systems, that is conventionally considered to be difficult for applying, with maintaining storage stability of a certain level or higher, and the use of the mixed pesticide composition in the present invention allows insect pest control of harmful pests within the soil to be efficiently conducted, and thus the present invention is extremely useful industrially.

The invention claimed is:

1. A mixed agrochemical emulsion composition comprising chloropicrin, a non-ionic surfactant and an organic phosphorous pesticide represented by the following formula (I):

Formula (I)

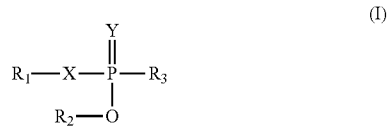

wherein $R_1$ represents a C1-4 linear or branched alkyl group; $R_2$ represents a C1-4 linear or branched alkyl group; $R_3$ represents a nitrogenated heterocyclic group which may have substituent(s) or a group of —$OR_4$ ($R_4$ represents a nitrogenated heterocyclic group which may have substituent(s)), X and Y each independently represent an oxygen atom or a sulfur atom, wherein either one of them is an oxygen atom, the other is a sulfur atom, and wherein the non-ionic surfactant is a non-ionic surfactant having a polyoxy C2-C4 alkylene aryl ether structure.

2. The mixed agrochemical emulsion composition according to claim 1, wherein the nitrogenated heterocyclic group in $R_3$ or $R_4$ is an imidazolidinyl group, a 1,3-thiazolidinyl group, a 1,3-oxazolidinyl group, a pyrazolyl group, an isoxazolyl group, a thiazolyl group, a pyridyl group, a pyrimidyl group, or a pyridazinyl group.

3. The mixed agrochemical emulsion composition according to claim 1, comprising: 0.1 to 80% by weight of the organic phosphorous pesticide, 10 to 90% by weight of chloropicrin, and 1 to 40% by weight of the non-ionic surfactant.

4. The mixed agrochemical emulsion composition according to claim 1, wherein the organic phosphorous pesticide is at least one or more selected from the group consisting of diazinon, fosthiazate, imicyafos, pyraclofos, chlorpyrifos and pirimiphos-methyl.

5. The mixed agrochemical emulsion composition according to claim 1, wherein the non-ionic surfactant having a polyoxy C2-C4 alkylene aryl ether structure is polyoxy C2-C4 alkylene aryl ether or formaldehyde condensate thereof.

6. The mixed agrochemical emulsion composition according to claim 1, wherein the aryl group in the polyoxy C2-C4 alkylene aryl ether structure is an unsubstituted phenyl group or C8-C12 alkyl substituted phenyl group, or a phenyl group substituted with phenyl group(s) or phenyl group(s) substituted with C1-C3 aliphatic group(s).

7. The mixed agrochemical emulsion composition according to claim 1, wherein the non-ionic surfactant having a polyoxy C2-C4 alkylene aryl ether structure is polyoxy C2-C4 alkylene phenyl substituted phenyl ether, polyoxy C2-C4 alkylene benzyl substituted phenyl ether, polyoxy C2-C4 alkylene styryl substituted phenyl ether, or polyoxy C2-C4 alkylene (unsubstituted phenyl, C8-C12 alkyl substituted phenyl or styryl substituted phenyl)ether formaldehyde condensate.

8. The mixed agrochemical emulsion composition according to claim 1, wherein the non-ionic surfactant is polyoxyethylene aryl ether or polyoxyethylene phenyl ether formaldehyde condensate.

9. The mixed agrochemical emulsion composition according to claim 1, wherein the non-ionic surfactant is polyoxy C2-C4 alkylene phenyl ether or aldehyde condensate thereof, polyoxy C2-C4 alkylene arylphenyl ether or formaldehyde condensate thereof, or polyoxy C2-C4 alkylene C8-C12 alkyl substituted phenyl ether formaldehyde condensate.

10. The mixed agrochemical emulsion composition according to claim 9, wherein the non-ionic surfactant is polyoxy C2-C4 alkylene phenyl ether formaldehyde condensate, or polyoxy C2-C4 alkylene arylphenyl ether, or formaldehyde condensate thereof.

11. The mixed agrochemical emulsion composition according to claim 1, wherein the number of repeating units of the polyoxy C2-C4 alkylene part in the polyoxy C2-C4 alkylene aryl ether structure is 10 to 25, provided that, in the case that the non-ionic surfactant having a polyoxy C2-C4 alkylene aryl ether structure is polyoxy C2-C4 alkylene aryl ether formaldehyde condensate, two molecules are bound so that the number of repeating units is the sum of the number of repeating units of polyoxy C2 to C4 alkylene parts.

12. The mixed agrochemical emulsion composition according to claim 1, further comprising epoxyglyceride or epoxidized vegetable oil.

13. The mixed agrochemical emulsion composition according to claim 12, further comprising an anionic surfactant.

14. The mixed agrochemical emulsion according to claim 1, wherein the organic phosphorous pesticide is fosthiazate or imicyafos.

15. The mixed agrochemical emulsion composition according to claim 1, wherein the organic phosphorous pesticide is fosthiazate or imicyafos, and polyoxy C2-C4 alkylene arylphenyl ether or formaldehyde condensate thereof or polyoxy C2-C4 alkylene phenyl ether formaldehyde condensate is contained as the non-ionic surfactant.

16. The mixed agrochemical emulsion according to claim 15, wherein the polyoxy C2-C4 alkylene arylphenyl ether is polyoxyethylene tristyrylphenyl ether, and polyoxy C2-C4 alkylene phenyl ether formaldehyde condensate is polyoxyethylene phenyl ether formaldehyde condensate.

17. The mixed agrochemical emulsion composition according to claim 14, further comprising epoxyglyceride or epoxidized vegetable oil.

18. The mixed agrochemical emulsion composition according to claim 17, comprising 0.3 to 10% by weight of fosthiazate or imicyafos, 70 to 90% by weight of chloropicrin, 5 to 30% by weight of polyoxy C2-C4 alkylene arylphenyl ether or formaldehyde condensate thereof, or polyoxy C2-C4 alkylene phenyl ether formaldehyde condensate, and 0.1 to 30% by weight of epoxyglyceride or epoxidized vegetable oil with respect to the total amount of the composition.

* * * * *